United States Patent [19]
Junino et al.

[11] Patent Number: 6,090,160
[45] Date of Patent: Jul. 18, 2000

[54] METHOD FOR DYEING KERATIN FIBERS WITH COMPOSITIONS WHICH CONTAIN 6- OR 7-HYDROXYINDOLE DERIVATIVES AS COUPLERS AND OXIDATION DYE PRECURSORS

[75] Inventors: Alex Junino, Livry-Gargan; Jean Jacques Vandenbossche, Aulnay-sous-Bois; Herve Richard, Paris; Jean Cotteret, Verneuil-sur-Seine, all of France

[73] Assignee: L'Oreal, France

[21] Appl. No.: 08/402,941

[22] Filed: Mar. 13, 1995

Related U.S. Application Data

[63] Continuation of application No. 07/901,142, Jun. 19, 1992, abandoned, which is a continuation of application No. 07/610,951, Nov. 9, 1990, abandoned.

[30] Foreign Application Priority Data

Nov. 10, 1989 [FR] France ................................ 89 14795

[51] Int. Cl.$^7$ ...................................................... A61K 7/13
[52] U.S. Cl. ........................ 8/409; 8/407; 8/408; 8/410; 8/423
[58] Field of Search ................................ 8/406, 407, 408, 8/409, 410, 412, 414, 416, 421, 423

[56] References Cited

U.S. PATENT DOCUMENTS

| | | | |
|---|---|---|---|
| 4,013,404 | 3/1977 | Parent et al. | 8/11 |
| 4,200,432 | 4/1980 | Kalopissis et al. | 8/409 |
| 4,277,244 | 7/1981 | Bugaut et al. | 8/411 |
| 4,425,132 | 1/1984 | Grollier et al. | 8/405 |
| 4,545,978 | 10/1985 | Kalopissis et al. | 8/405 |
| 4,776,857 | 10/1988 | Carroll et al. | 8/405 |
| 4,932,977 | 6/1990 | Schultz | 8/407 |
| 5,021,067 | 6/1991 | Grollier | 8/409 |
| 5,131,911 | 7/1992 | Lang et al. | 8/405 |
| 5,279,620 | 1/1994 | Junino et al. | 8/423 |

FOREIGN PATENT DOCUMENTS

| | | |
|---|---|---|
| 2626771 | 2/1989 | France . |
| 2636237 | 9/1989 | France . |
| 3031709 | 4/1982 | Germany . |
| 2207443 | 2/1989 | United Kingdom . |
| 2211517 | 7/1989 | United Kingdom . |

*Primary Examiner*—Caroline D. Liott
*Attorney, Agent, or Firm*—Cushman Darby & Cushman IP of Pillsbury Madison & Sutro

[57] ABSTRACT

Hydraulic coupler compounds corresponding to the formula:

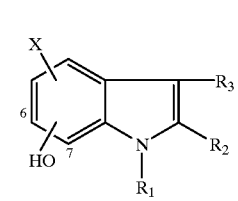

(I)

in which $R_1$ denotes a hydrogen atom or a $C_1$–$C_4$ alkyl radical; $R_2$ and $R_3$, which may be identical or different, denote a hydrogen atom, a $C_1$–$C_4$ lower alkyl radical, a carboxyl radical or an alkoxycarbonyl radical; X denotes a $C_1$–$C_4$ lower alkyl radical, a $C_1$–$C_{18}$ alkoxy radical, a halogen atom, a $C_1$–$C_{20}$ acyloxy radical, an acetylamino group, a trimethylsilyloxy group or a dialkyl($C_1$–$C_4$) aminomethyl group, the OH group occupying the 6- or 7-positions, as well as their salts, are combined with oxidation dye precursors for dyeing keratinous fibers.

17 Claims, No Drawings

METHOD FOR DYEING KERATIN FIBERS WITH COMPOSITIONS WHICH CONTAIN 6- OR 7-HYDROXYINDOLE DERIVATIVES AS COUPLERS AND OXIDATION DYE PRECURSORS

This is a continuation of application Ser. No. 07/901,142, filed Jun. 19, 1992, now abandoned, which is a continuation of application Ser. No. 07/610,951, filed Nov. 9, 1990, now abandoned.

The present invention relates to new tinctorial compositions for keratinous fibers and in particular for human hair, containing oxidation dye precursors and couplers derived from 6- or 7-hydroxyindole, and a dyeing method using such compositions.

It is known to dye keratinous fibers, and in particular human hair, with tinctorial compositions containing oxidation dye precursors and in particular p-phenylenediamines or ortho- or para-aminophenols, which are generally termed "oxidation bases".

It is also known that the hues obtained with these oxidation bases can be varied by combining them with couplers, also termed coloring modifiers, chosen in particular from aromatic meta-diamines, meta-aminophenols and meta-diphenols.

In the field of hair dyeing, oxidation dye precursors or couplers are sought which enable a coloring having a satisfactory resistance to light, to washing, to the weather and to perspiration to be imparted to the hair, in an oxidizing alkaline medium generally used in oxidation dyeing.

The applicants have just discovered, and it is this which is the subject of the invention, that the use of certain 6- or 7-hydroxyindole derivatives as couplers, with oxidation dye precursors, enabled dyeings having particularly surprising resistance to light, to washing, to the weather and to perspiration to be obtained after application to the keratinous fibers and in particular the hair, in particular when they are used with p-phenylenediamine and its derivatives. This use therefore comprises one subject of the invention.

The invention also relates to oxidation tinctorial compositions, intended to be used for dyeing keratinous fibers, containing at least one oxidation dye precursor of the para and/or ortho type with certain indole derivatives defined below.

Another subject of the invention comprises the method for dyeing keratinous fibers, in particular human hair, using such compositions.

Further subjects of the invention will become apparent on reading the description and the examples which follow.

The compounds derived from 6- or 7-hydroxyindole which are used as couplers in the oxidation dyeing of keratinous fibers and in particular of human hair, in the presence of at least one para and/or ortho oxidation dye precursor, correspond to the formula:

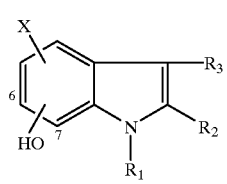

(I)

in which $R_1$ denotes a hydrogen atom or a $C_1$–$C_4$ alkyl radical; $R_2$ and $R_3$, which may be identical or different, denote a hydrogen atom, a $C_1$–$C_4$ lower alkyl radical, a carboxyl radical or an alkoxycarbonyl radical; X denotes a $C_1$–$C_4$ lower alkyl radical, a $C_1$–$C_{18}$ alkoxy radical, a halogen atom, a $C_1$–$C_{20}$ acyloxy radical, an acetylamino group, a trimethylsilyloxy group or a dialkyl($C_1$–$C_4$) aminomethyl group; the OH group occupying the 6- or 7-position of the aromatic ring; as well as their salts.

Amongst the compounds of formula (I), the preferred compounds are the compounds in which the alkyl radical denotes methyl or ethyl; the alkoxycarbonyl radical denotes methoxycarbonyl or ethoxycarbonyl; the alkoxy radical denotes methoxy, ethoxy, butoxy or hexadecyloxy; and the acyloxy radical denotes acetoxy or tetradecanoyloxy.

Amongst these compounds, those which may be mentioned are 6-hydroxy-5-acetoxyindole, 6-hydroxy-5-methoxyindole, 6-hydroxy-5-methoxy-2-methylindole, 6-hydroxy-5-butoxyindole, 6-hydroxy-5-methoxyindole-2-carboxylic acid, 6-hydroxy-7-methoxyindole, 6-hydroxy-5-methoxy-2,3-dimethylindole, 7-hydroxy-4-methoxy-2,3-dimethylindole, 6-hydroxy-5-tetradecanoyloxyindole, 6-hydroxy-5-hexadecyloxyindole, 6-hydroxy-5-butanoyloxyindole, 6-hydroxy-5-oleyloxyindole, 6-hydroxy-5-ethanoyloxyindole, 6-hydroxy-5-hexanoyloxyindole, 6-hydroxy-5-pivaloyloxyindole, 6-hydroxy-5-formyloxyindole, 6-hydroxy-5-trimethylsilyloxyindole, 6-hydroxy-7-methylindole, 7-hydroxy-6-dimethylaminomethylindole, 7-hydroxy-6-methoxy-2-methylindole 6-hydroxy-7-methoxy-2-ethoxycarbonylindole, 6-hydroxy-7-dimethylaminomethylindole, 6-hydroxy-3,7-dimethylindole, 6-hydroxy-3-methyl-7-dimethylaminomethylindole, 6-hydroxy-5-methoxy-1-methylindole, 6-hydroxy-5-methyl-2-carboxyindole, -6-hydroxy-7-methoxy-2-methylindole, 6-hydroxy-5-methoxy-2-methylindole, 6-hydroxy-5-acetylamino-2,3-dimethylindole.

6-Hydroxy-5-acetylamino-2,3-dimethylindole is a new compound and constitutes another subject of the invention.

The dye precursors of para or ortho type are compounds which are not themselves dyes but which form a dye by an oxidative condensation process, either on themselves or in the presence of a coupler or modifier.

These compounds contain functional groups, these being either two amino or one amino and one hydroxy, in the para or ortho position, the one relative to the other.

The precursors of para type are in particular chosen from paraphenylenediamines, para-aminophenols, para heterocyclic precursors, such as 2,5-diaminopyridine, 2-hydroxy-5-aminopyridine and tetraaminopyrimidine and the so-called "double" bases.

Paraphenylenediamines which may be mentioned are the compounds corresponding to the formula (II) below

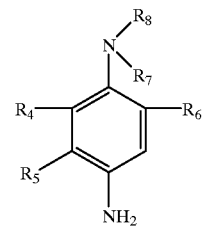

(II)

in which $R_4$, $R_5$ and $R_6$, which may be identical or different, represent a hydrogen or halogen atom, an alkyl radical having 1 to 4 carbon atoms or an alkoxy radical having 1 to 4 carbon atoms, and $R_7$ and $R_8$, which may be identical or different, represent a hydrogen atom or an alkyl, hydroxyalkyl, alkoxyalkyl, carbamylalkyl, mesylaminoalkyl, acetylaminoalkyl, ureidoalkyl, carbalkoxyaminoalkyl, piperidinoalkyl or morpholinoalkyl radical, these alkyl or alkoxy groups having from 1 to 4 carbon atoms, or $R_7$ and $R_8$ form, together with the nitrogen atom to which they are bonded, a piperidino or morpholino heterocycle, with the proviso that $R_4$ or $R_6$ represents a hydrogen atom when $R_7$ and $R_8$ do not represent a hydrogen atom, as well as the salts of these compounds.

Amongst the compounds of formula (II), the following may be mentioned: p-phenylenediamine, p-toluylenediamine, methoxyparaphenylenediamine, chloroparaphenylenediamine, 2,6-dimethylparaphenylenediamine, 2,5-dimethylparaphenylenediamine, 2-methyl-5-methoxyparaphenylenediamine, 2,6-dimethyl-5-methoxyparaphenylenediamine, N,N-dimethylparaphenylenediamine, 3-methyl-4-amino-N,N-diethylaniline, N,N-di(β-hydroxyethyl)paraphenylenediamine, 3-methyl-4-amino-N,N-di-(βhydroxyethyl)aniline, 3-chloro-4-amino-N,N-di-(β-hydroxyethyl)aniline, 4-amino-N,N(ethyl,carbamylmethyl) aniline, 3-methyl-4-amino-N,N-(ethyl,carbamylmethyl) aniline, 4-amino-N,N-(ethyl,β-piperidinoethyl)aniline, 3-methyl-4-amino-N,N-(ethyl,β-piperidinoethyl)aniline, 4-amino-N,N-(ethyl,β-morpholinoethyl)aniline, 3-methyl-4-amino-N,N-(ethyl,β-morpholinoethyl)aniline, 4-amino-N, N-(ethyl,β-acetylaminoethyl)aniline, 4-amino-N-(β-methoxyethyl)aniline, 3-methyl-4-amino-N,N-(ethyl,β-acetylaminoethyl)aniline, 4-amino-N,N-(ethyl,β-mesylaminoethyl)aniline, 3-methyl-4-amino-N,N-(ethyl,β-mesylaminoethyl)aniline, 4-amino-N,N-(ethyl,β-sulphoethyl)aniline, 3-methyl-4-amino-N,N-(ethyl,β-sulphoethyl)aniline, N-[(4'-amino)phenyl]morpholine and N-[(4'-amino)phenyl]piperidine.

These oxidation dye precursors of para type can be introduced into the tinctorial composition either in the form of the free base or in the form of salts, such as in the form of the hydrochloride, hydrobromide or sulphate.

Amongst the p-aminophenols, the following may be mentioned: p-aminophenol, 2-methyl-4-aminophenol, 3-methyl-4-aminophenol, 2-chloro-4-aminophenol, 3-chloro-4-aminophenol, 2,6-dimethyl-4-aminophenol, 3,5-dimethyl-4-aminophenol, 2,3-dimethyl-4-aminophenol, 2-hydroxymethyl-4-aminophenol, 2-(β-hydroxyethyl)-4-aminophenol, 2-methoxy-4-aminophenol, 3-methoxy-4-aminophenol, 2,5-dimethyl-4-aminophenol and 2-methoxymethyl-4-aminophenol.

The oxidation dyes of ortho type are chosen from ortho-aminophenols, such as 1-amino-2-hydroxybenzene, 6-methyl-1-hydroxy-2-aminobenzene and 4-methyl-1-amino-2-hydroxybenzene, and orthophenylenediamines.

The so-called double bases are bis-phenylalkylenediamines corresponding to the formula:

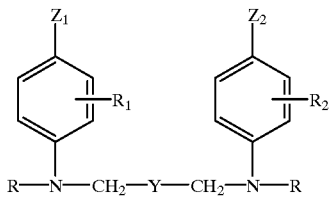

(III)

in which:

$Z_1$ and $Z_2$, which may be identical or different, represent hydroxyl or $NHR_3$ groups, where $R_3$ denotes a hydrogen atom or a lower alkyl radical;

$R_1$ and $R_2$, which may be identical or different, represent either hydrogen atoms or halogen atoms or alkyl groups;

R represents a hydrogen atom or an alkyl, hydroxyalkyl or aminoalkyl group, in which the amino radical can be substituted; and Y represents a radical taken from the group comprising the following radicals:

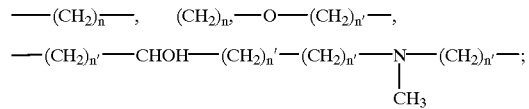

n being an integer between 0 and 8 and n' being an integer between 0 and 4, it being possible for this base to be in the form of its addition salts with acids.

The alkyl or alkoxy radicals preferably denote a group having 1 to 4 carbon atoms and in particular methyl, ethyl or propyl or methoxy or ethoxy.

Amongst the compounds of formula (III), the following may be mentioned: N,N'-bis(β-hydroxyethyl)-N,N'-bis(4'-aminophenyl)-1,3-diaminopropan-2-ol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine and N,N'-bis(ethyl)-N,N'-bis(4'-amino-3'-methylphenyl)ethylenediamine.

In addition to the heterocyclic coupler from the family of 6- or 7-hydroxyindoles of formula (I) defined above, it is optionally also possible to use other couplers known per se, such as metadiphenols, meta-aminophenols, metaphenylenediamines, meta-acylaminophenols, meta-ureidophenols, metacarbalkoxyaminophenols, α-naphthol and couplers having an active methylene group, such as the β-ketone compounds, pyrazolones or 4-hydroxyindole.

Amongst these couplers, the following may be mentioned more particularly: 2,4-dihydroxyphenoxyethanol, 2,4-dihydroxyanisole, meta-aminophenol, resorcinol monomethyl ether, 2-methyl-5-N-(β-hydroxyethyl)-aminophenol, 2-methyl-5-N-(β-mesylaminoethyl)-aminophenol, 6-hydroxybenzomorpholine, 2,4-diaminoanisole, 2,4-diaminophenoxyethanol, 6-aminobenzomorpholine, [2-N-(β-hydroxyethyl)amino-4-amino]-phenoxyethanol, 2-amino-4-N-(β-hydroxyethyl)aminoanisole, 2,4-diaminophenyl β, γ-dihydroxypropyl ether, 2,4-diaminophenoxyethylamine, 1,3-dimethoxy-2,4-diaminobenzene, 2-methyl-5-aminophenol and 2,6-dimethyl-3-aminophenol and their salts.

As is well known in the state of the art, direct dyes, such as azo or anthraquinone dyes or the nitro derivatives of the benzene series, may be used together with the abovementioned compounds, in particular with a view to shading, or enriching with glints, the colorings imparted by the oxidation dye precursors and the coupler of formula (I).

Neither any derivative of the family of benzoquinones or naphthoquinones which is capable of oxidizing the compound of formula (I) nor the iodide ion is used together with the couplers of formula (I).

The abovementioned compounds are used with the aid of oxidation tinctorial compositions containing, in a medium appropriate for dyeing, at least one para and/or ortho oxidation dye precursor and at least, as coupler, the 6- or 7-hydroxyindole derivative of formula (I) defined above, as well as, optionally, the other couplers and/or other direct dyes.

These compositions must not contain iodide ions in proportions capable of oxidizing the precursor and the coupler of formula (I).

The tinctorial compositions which constitute another subject of the invention are essentially characterized in that they contain, in a medium appropriate for dyeing:

a) at least one coupler of formula (I), and b) at least one para and/or ortho oxidation dye precursor chosen from para-aminophenols, heterocyclic precursors, ortho-aminophenols, orthophenylenediamines, the so-called "double" bases as defined above, and paraphenylenediamines of formula (IV):

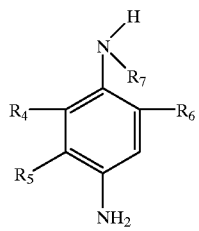

in which $R_4$, $R_5$ and $R_6$, which may be identical or different, represent a hydrogen or halogen atom, an alkyl radical having 1 to 4 carbon atoms or an alkoxy radical having 1 to 4 carbon atoms, and $R_7$ represents a hydrogen atom or an alkyl, carbamylalkyl, mesylaminoalkyl, acetylaminoalkyl, ureidoalkyl, carbalkoxyaminoalkyl, piperidinoalkyl or morpholinoalkyl radical, these alkyl or alkoxy groups having from 1 to 4 carbon atoms, as well as the salts of these compounds.

Amongst the compounds of formula (IV), those which may be mentioned are: p-phenylenediamine, p-toluylenediamine, methoxyparaphenylenediamine, chloroparaphenylenediamine, 2,6-dimethylparaphenylenediamine, 2,5-dimethylparaphenylenediamine, 2-methyl-5-methoxyparaphenylenediamine and 2,6-dimethyl-5-methoxyparaphenylenediamine.

These oxidation dye precursors of para type can be introduced into the tinctorial composition either in the form of the free base or in the form of salts, such as in the form of the hydrochloride, hydrobromide or sulphate.

These compositions do not contain iodide ions in amounts capable of oxidizing the precursors and couplers present.

The oxidation dye precursors of para and/or ortho type and the couplers used in the tinctorial compositions according to the invention preferably represent, as a whole, from 0.3 to 7% by weight relative to the weight of the said composition. The concentration of compounds (I) may vary between 0.05 and 3.5% by weight relative to the total weight of the composition.

The medium appropriate for dyeing is generally an aqueous medium and its pH may vary between 8 and 11 and is preferably between 9 and 11.

It is adjusted to the desired value with the aid of an alkalinizing agent, such as ammonia, alkali metal carbonates and alkanolamines, such as mono-, di- or tri-ethanolamine.

The tinctorial compositions according to the invention also contain, in their preferred embodiment, anionic, cationic, nonionic or amphoteric surfactants or their mixtures. Amongst these surfactants, the following may be mentioned: fatty alcohol alkylbenzenesulphonates, alkylnaphthalenesulphonates, sulphates, ether-sulphates and sulphonates, quaternary ammonium salts, such as trimethylcetylammonium bromide and cetylpyridinium bromide, optionally oxyethylenated fatty acid ethanolamides; polyoxyethylenated acids, alcohols or amines, polyglycerolated alcohols, polyoxyethylenated or polyglycerolated alkylphenols and polyoxyethylenated alkyl sulphates.

These surfactants are present in the compositions according to the invention in proportions of between 0.5 and 55% by weight, and preferably between 2 and 50% by weight, relative to the total weight of the composition.

These compositions may also contain organic solvents to dissolve the compounds which would not be sufficiently soluble in water. Amongst these solvents, the following may be mentioned by way of example: $C_1$–$C_4$ lower alkanols, such as ethanol and isopropanol; glycerol; glycols or glycol ethers, such as 2-butoxyethanol, ethylene glycol, propylene glycol and diethylene glycol monoethyl ether and monomethyl ether, and also aromatic alcohols, such as benzyl alcohol or phenoxyethanol and the analogous products or their mixtures.

The solvents are preferably present in proportions of between 1 and 40% by weight and in particular between 5 and 30% by weight, relative to the total weight of the composition.

The thickeners which may be added to the compositions according to the invention may be chosen from sodium alginate, gum arabic, cellulose derivatives, acrylic acid polymers and xanthan gum. Inorganic thickeners may also be used, such as bentonite.

These thickeners are preferably present in proportions of between 0.1 and 5% and in particular between 0.2 and 3% by weight, relative to the total weight of the composition.

The antioxidants which may be present in the compositions are chosen, in particular, from sodium sulphite, thioglycolic acid, sodium bisulphite, ascorbic acid, hydroquinone and homogentisic acid. These antioxidants are present in the composition in proportions of between 0.05 and 1.5% by weight, relative to the total weight of the composition.

These compositions may also contain other cosmetically acceptable adjuvants, such as, for example, penetration agents, sequestering agents, perfumes, buffers, etc.

The compositions according to the invention may be in various forms, such as in the form of liquids, creams or gels or in any other form appropriate for effecting a dyeing of keratinous fibers and in particular of human hair. These compositions may be packaged in aerosol bottles in the presence of a propellant.

The method, according to the invention, for dyeing keratinous fibers and in particular human hair uses development by hydrogen peroxide.

In accordance with this method, a composition, prepared at the time of use, containing at least one coupler of formula (I), at least one para and/or ortho oxidation dye precursor and at least one oxidizing solution based on hydrogen peroxide is applied to the keratinous fibers in an amount sufficient to be able to develop a colouring.

A 20-volume hydrogen peroxide solution is preferably used. The mixture obtained is applied to the hair and is left on the hair for 10 to 40 minutes, preferably 15 to 30 minutes, after which the hair is rinsed, optionally washed with shampoo and rinsed again, and dried.

The heterocyclic coupler from the family of 6- or 7-hydroxyindoles of formula (I) defined above may also be used in a multi-step method consisting, in one of the steps, in applying the para and/or ortho oxidation dye precursor and, in another step, in applying the coupler of formula (I).

The oxidizing agent can be introduced just before the application of the composition applied in the second step or can be added to the keratinous fibers in a third step, the conditions for exposure and drying or washing being similar to those indicated above.

The examples which follow are intended to illustrate the invention without any limitation being implied.

The following composition is prepared:

COMPOSITION A

| Dyes | x g |
|---|---|
| Octyidodecanol sold under the name EUTANOL G by HENKEL | 8.0 g |
| Oleic acid | 20.0 g |
| Monoethanolamine lauryl ether sulphate sold under the name SIPON LM 35 by HENKEL | 3.0 g |
| Ethyl alcohol | 10.0 g |
| Benzyl alcohol | 10.0 g |
| Cetylstearyl alcohol containing 33 moles of ethylene oxide, sold under the name SIMULSOL GS by SEPPIC | 2.4 g |
| Ethylenediaminetetraacetic acid | 0.2 g |
| Cationic polymer consisting of recurring units: | 2.2 g |
| 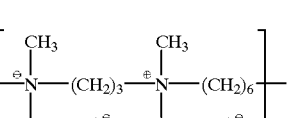 | |
| Monoethanolamine | 7.5 g |
| Linoleic acid diethanolamide sold under the name COMPERLAN F by HENKEL | 8.0 g |
| Ammonia containing 20% $NH_3$ | 10.2 g |
| 35% aqueous sodium metabisulphite solution | 1.3 g |
| Hydroquinone | 0.15 g |
| 1-Phenyl-3-methyl-5-pyrazolone | 0.20 g |
| Demineralized water qs | 100.0 g |

In all of the examples which follow, the dyes are introduced in the amounts indicated in the table. The composition containing the dye is mixed weight for weight with an oxidizing agent assaying 20-volume hydrogen peroxide and having a pH of 3.

The mixtures thus produced are applied for 30 minutes to grey hair which is 90% white and the hair is then rinsed, washed, rinsed again and dried.

TABLE I

| Examples | Heterocyclic coupler of formula (I) | g | Para precursor | g | Color |
|---|---|---|---|---|---|
| 1 | 2,3-dimethyl-5-methoxy-6-hydroxy-indole | 0.382 | p-phenylenediamine | 0.216 | light ash blonde |
| 2 | 5-methoxy-6-hydroxyindole | 0.652 | p-aminophenol | 0.436 | light ash blonde |
| 3 | 7-methoxy-6-hydroxyindole | 0.326 | p-phenylene diamine | 0.216 | coppery golden ash blonde |
| 4 | 7-methoxy-6-hydroxyindole | 0.652 | p-aminophenol | 0.436 | coppery golden blonde |
| 5 | 5-tetradecanoyloxy-6-hydroxyindole | 1.438 | p-aminophenol | 0.436 | warm chestnut deep blonde |
| 6 | 5-acetoxy-6-hydroxyindole | 0.765 | p-aminophenol | 0.436 | warm chestnut deep blonde |
| 7 | 2-methyl-5-methoxy-6-hydroxyindole | 0.354 | p-phenylene-diamine | 0.216 | light beige blonde |
| 8 | 2,3-dimethyl-4-methoxy-7-hydroxyindole | 0.382 | p-phenylene-diamine | 0.216 | pearly beige blonde |

TABLE II

| Examples | Heterocyclic coupler of formula (I) | g | Para precursor | g | Color |
|---|---|---|---|---|---|
| 9 | 2,3-dimethyl-4-methoxy-7-hydroxyindole | 0.764 | p-aminophenyl | 0.436 | beige coppery blonde |
| 10 | 6-hydroxy-5-butanoyl-oxyindole | 0.438 | p-phenylene-diamine | 0.216 | golden ash blonde |
| 11 | 6-hydroxy-7-methyl-indole | 0.294 | p-phenylene-diamine | 0.216 | coppery golden blonde |
| 12 | 6-hydroxy-7-methyl-indole | 0.588 | paraaminophenyl | 0.438 | coppery blonde |
| 13 | 7-hydroxy-4-methoxy-2,3-dimethylindole | 0.764 | paraaminophenol | 0.438 | pearly beige light blonde |
| 14 | 6-hydroxy-5-methoxy-1-methylindole | 0.708 | paraaminophenol | 0.438 | pearly deep auburn |
| 15 | 6-hydroxy-5-methyl-2-carboxylindole | 0.76 | paraaminophenol | 0.438 | golden copper |

Dying Example No. 16

The following tinctorial mixture is prepared:

0.545 g of 5-acetamido-2,3-dimethyl-6-hydroxyindole
0.270 g of paraphenylenediamine
polyglycerolated oleyl alcohol containing 2 moles of glycerol 4.5 g
polyglycerolated oleyl alcohol containing 4 moles of glycerol 4.5 g
ETHOMEEN O 12—ARMOON HESS CHEMICAL Ltd. (oxyethylenated oleylamine containing 12 moles of E.O.) 4.5 g
COMPERLAN KD—HENKEL (copra diethanolamide) 9 g
propylene glycol 4 g
2-butoxyethanol 8 g
96° ethanol 6 g
MASQUOL DTPA—PROTEX (pentasodium salt of diethylenetriaminepentaacetic acid). 2 g
hydroquinone 0.15 g
35° Bé sodium bisulphite solution 1.3 g
22° Bé ammonia 10 g
water qs 100 g At the time of use, 20-volume hydrogen peroxide is added weight for weight. The mixture, applied for 30 minutes at ambient temperature to natural hair which is 90% white, imparts a chestnut coloring thereto after shampooing and rinsing.

EXAMPLE

Synthesis of 5-acetylamino-2,3-dimethyl-6-hydroxyindole

A solution of 41.3 g of sodium sulphite in 130 ml of water is added to a solution of 50.7 g of 5-amino-2,3-dimethyl-6-hydroxyindole in 250 ml of water at ambient temperature.

15.6 ml of acetic anhydride are added in a single amount. After stirring for one hour, the suspension is cooled and the precipitate is filtered off; the solid is drained to neutral pH and dried.

Analysis of the product, recrystallized from isopropanol, gives the following results:

m.p.=217° C.

elementary analysis for $C_{12} H_{14} N_2 O_2$.

|  | C | H | N | O |
|---|---|---|---|---|
| calculated | 66.03 | 6.47 | 12.84 | 14.66 |
| found | 65.90 | 6.50 | 12.67 | 14.93 |

We claim:

1. In a tinctorial composition for dyeing keratinous fibers which comprises, in a medium suitable for dyeing said fibers, at least one oxidation dyestuff precursor selected from the group consisting of a paraphenylene diamine having the formula

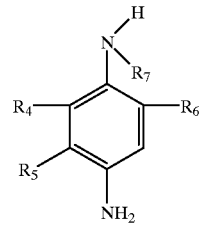

(IV)

wherein $R_4$, $R_5$ and $R_6$, each independently represent hydrogen, halogen, an alkyl having 1–4 carbon atoms or alkoxy having 1–4 carbon atoms, and $R_7$ represents hydrogen, alkyl, carbamylalkyl, mesylaminoalkyl, acetylaminoalkyl, ureidoalkyl, carbalkoxyaminoalkyl, piperidinoalkyl or morpholinoalkyl, wherein said alkyl and alkoxy moieties have 1–4 carbon atoms, and the salt of said paraphenylenediamine, a para-aminophenol, a para-heterocyclic oxidation dye precursor, a bis-phenyl alkylene diamine, an ortho-aminophenol and an ortho-phenylenediamene, and at least one oxidizing agent containing hydrogen peroxide, the improvement comprising including in said composition at least one heterocyclic coupler having the formula

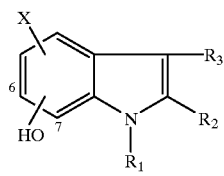

(I)

wherein
- $R_1$ represents hydrogen or $C_1$–$C_4$ alkyl, $R_2$ and $R_3$, each independently, represent hydrogen, $C_1$–$C_4$ lower alkyl, carboxyl or alkoxycarbonyl, X represents $C_1$–$C_4$ lower alkyl, $C_1$–$C_{18}$ alkoxy, halogen, $C_1$–$C_{20}$ acyloxy, acetylamino, trimethylsilyloxy or di($C_1$–$C_4$) alkylaminomethyl,
- the OH group occupying the 6- or 7-positions,
- and the salts thereof,
- said heterocyclic coupler being present in an amount ranging from 0.05 to 3.5 percent by weight based on the total weight of said composition,
- the combined total weight of said oxidation dyestuff precursor and said heterocyclic coupler ranging from 0.3 to 7 weight percent based on the total weight of said composition,
- said composition being free of any iodide ions in an amount capable of oxidizing said oxidation dyestuff precursor and said heterocyclic coupler of formula I.

2. The tinctorial composition of claim 1 wherein said coupler of formula (I) is selected from the group consisting of
6-hydroxy-5-acetoxyindole,
6-hydroxy-5-methoxyindole,
6-hydroxy-5-methoxy-2-methylindole,
6-hydroxy-5-butoxyindole,
6-hydroxy-5-methoxyindole-2-carboxylic acid,
6-hydroxy-7-methoxyindole,
6-hydroxy-5-methoxy-2,3-dimethylindole,
7-hydroxy-4-methoxy-2,3-dimethylindole,
6-hydroxy-5-tetradecanoyloxyindole,
6-hydroxy-5-hexadecyloxyindole,
6-hydroxy-5-butanoyloxyindole,
6-hydroxy-5-oleyloxyindole,
6-hydroxy-5-ethanoyloxyindole,
6-hydroxy-5-hexanoyloxyindole,
6-hydroxy-5-pivaloyloxyindole,
6-hydroxy-5-formyloxyindole,
6-hydroxy-5-trimethylsilyloxyindole,
6-hydroxy-7-methylindole,
7-hydroxy-6-dimethylaminomethylindole,
7-hydroxy-6-methoxy-2-methylindole,
6-hydroxy-7-methoxy-2-ethoxycarbonylindole,
6-hydroxy-7-dimethylaminomethylindole,
6-hydroxy-3,7-dimethylindole,
6-hydroxy-3-methyl-7-dimethylaminomethylindole,
6-hydroxy-5-methoxy-1-methylindole,
6-hydroxy-5-methyl-2-carboxyindole,
6-hydroxy-7-methoxy-2-methylindole,
6-hydroxy-5-methoxy-2-methylindole and
6-hydroxy-5-acetylamino-2,3-dimethylindole.

3. The tinctorial composition of claim 1 wherein said paraphenylenediamine is selected from the group consisting of
paraphenylenediamine,
paratoluylenediamine,
methoxyparaphenylenediamine,
chloroparaphenylenediamine,
2,6-dimethylparaphenylenediamine,
2,5-dimethylparaphenylenediamine,
2-methyl-5-methoxyparaphenylenediamine, and
2,6-dimethyl-5-methoxyparaphenylenediamine.

4. The tinctorial composition of claim 1 wherein said para aminophenol is selected from the group consisting of para aminophenol,
2-methyl-4-aminophenol,
3-methyl-4-aminophenol,
2-chloro-4-aminophenol,
3-chloro-4-aminophenol,
2,6-dimethyl-4-aminophenol,
3,5-dimethyl-4-aminophenol,
2,3-dimethyl-4-aminophenol,
2-hydroxymethyl-4-aminophenol,
2-(β-hydroxyethyl)-4-aminophenol,
2-methoxy-4-aminophenol,
3-methoxy-4-aminophenol,
2-methoxymethyl-4-aminophenol and
2,5-dimethyl-4-aminophenol.

5. The tinctorial composition of claim 1 wherein said bis-phenylalkylene diamine has the formula

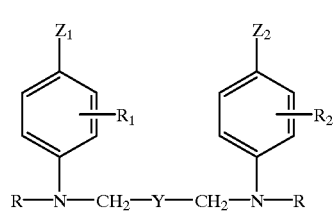

(III)

wherein
- $Z_1$ and $Z_2$, each independently, represent hydroxyl or $NHR_3$ wherein $R_3$ represents hydrogen or lower alkyl,
- $R_1$ and $R_2$, each independently, represent hydrogen, halogen or alkyl,
- R represents hydrogen, alkyl, hydroxyalkyl or aminoalkyl wherein the amino moiety is substituted or unsubstituted, and
- Y represents a member selected from the group consisting of

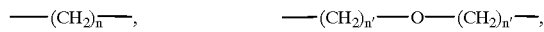

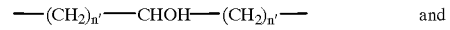   and

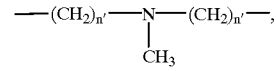

wherein n is an integer ranging from 0 to 8 and n' is an integer ranging from 0 to 4, and
the acid addition salt of said bis-phenylalkylene-diamine.

6. The tinctorial composition of claim 5 wherein said bis-phenylalkylenediamine of formula III is selected from the group consisting of
N,N'-bis(β-hydroxyethyl)-N,N'-bis(4'-aminophenyl)-1,3-diaminopropan-2-ol,
N,N'-bis(β-hydroxyethyl)-N,N'-bis(4'-aminophenyl)ethylenediamine,
N,N'-bis(4-aminophenyl)-tetramethylenediamine,
N,N'-bis(β-hydroxyethyl)-N,N'-bis(4-aminophenyl)tetramethylenediamine, N,N'-bis(4-methylaminophenyl)tetramethylenediamine and N,N'-bis(ethyl)-N,N'-bis(4-amino-3'-methylphenyl) ethylenediamine.

7. The tinctorial composition of claim 1 which also contains, in addition to the heterocyclic coupler of formula (I), a metadiphenol, a metaaminophenol, a metaphenylenediamine, a meta-acylaminophenol, a meta-ureidophenol, a meta carbalkoxyaminophenol, α-naphthol, a β-keto compound, a pyrazolone or 4-hydroxyindole.

8. The tinctorial composition of claim 1 which also contains a direct dye.

9. The tinctorial composition of claim 1 wherein said medium suitable for dyeing said fibers is an aqueous medium having a pH ranging from 8 to 11.

10. The tinctorial composition of claim 1 which also contains an anionic, cationic, nonionic or amphoteric surfactant or a mixture thereof.

11. The tinctorial composition of claim 1 which also contains an organic solvent present in an amount ranging from 1 to 40 percent by weight based on the total weight of said composition.

12. The tinctorial composition of claim 1 which also contains one or more of a thickener, an antioxidant, a penetration agent, a sequestering agent, a buffer and a perfume.

13. The tinctorial composition of claim 1 in the form of a liquid, a cream, a gel or an aerosol packaged in the presence of a propellant.

14. A method for dyeing keratinous fibers comprising applying to said fibers a tinctorial composition comprising in a medium suitable for dyeing said fibers at lease one oxidation dyestuff precursor selected from the group consisting of a paraphenylene diamine having the formula

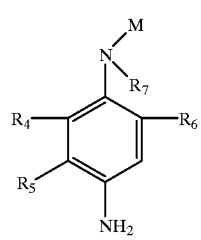

(IV)

wherein $R_4$, $R_5$ and $R_6$ each independently represent hydrogen, halogen, an alkyl having 1–4 carbon atom or alkoxy having 1–4 carbon atoms, and $R_7$ represents hydrogen alkyl carbamylalkyl mesylaminoalkyl, acetylaminoalkyl, ureidoalkyl, carbalkoxyaminoalkyl, piperidinoalkyl or morpholinoalkyl wherein said alkyl and alkoxy moieties have 1–4 carbon atoms, and the salt of said paraphenylenediamine, a para-aminophenol, a para heterocyclic oxidation dye precursor, a bis-phenyl alkylene diamine, an ortho aminophenol and an ortho phenylenediamine, in combination with at least one heterocyclic coupler having the formula

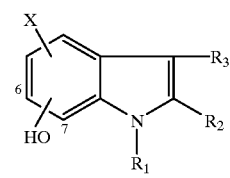

(I)

wherein $R_1$ represents hydrogen or $C_1$–$C_4$ alkyl, $R_2$ and $R_3$, each independently, represent hydrogen, $C_1$–$C_4$ lower alkyl, carboxyl or alkoxycarbonyl, X represents $C_1$–$C_4$ lower alkyl, $C_1$–$C_{18}$ alkoxy, halogen, $C_1$–$C_{20}$acyloxy, acetylamino, trimethylsilyloxy or di($C_1$–$C_4$) alkylaminomethyl, the OH group occupying the 6- or 7-positions, and the salts thereof, said heterocyclic coupler being present in an amount ranging from 0.05 to 3.5 percent by weight based on the total weight said composition, the combined total weight of said oxidation dyestuff precursor and said heterocyclic coupler ranging from 0.3 to 7 weight percent based on the total weight of said composition, and at least one oxidizing agent containing hydrogen peroxide said composition being free of any iodide ions in an amount capable of oxidizing said oxidation dyestuff precursor and said heterocyclic coupler of formula (I), permitting said tinctorial composition to remain in contact with said keratinous fibers for a period of time ranging from 10 to 40 minutes, rinsing said keratinous fibers, optionally washing said keratinous fibers, and drying said keratinous fibers.

15. A method for dyeing keratinous fibers comprising in a first step applying to said keratinous fibers a first composition comprising in a medium suitable for dyeing said fibers at least one oxidation dyestuff precursor selected from the group consisting of a paraphenylene diamine having the formula

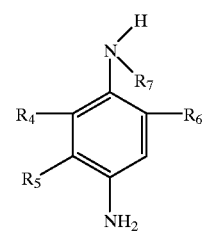

(IV)

wherein $R_4$, $R_5$ and $R_6$ each independently represent hydrogen halogen, and alkyl having 1–4 carbon atoms or alkoxy having 1–4 carbon atoms, and $R_7$ represents hydrogen, alkyl, carbamylalkyl, mesylaminoalkyl, acetylaminoalkyl, ureidoalkyl, carbalkoxyaminoalkyl, piperidinoalkyl or morpholinoalkyl, wherein said alkyl and alkoxy moieties have 1–4 carbon atoms, and the salt of said paraphenylenediamine, a para-aminophenol, a para heterocyclic oxidation dye precursor, a bis-phenyl alkylenediamine, an ortho aminophenol and an ortho-phenylenediamine, in a second step applying to said keratinous fibers a second composition comprising in a medium suitable for dyeing said fibers at least one heterocyclic coupler having the formula

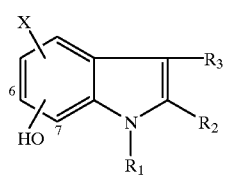

(I)

wherein $R_1$ represents hydrogen or $C_1$–$C_4$ alkyl, $R_2$ and $R_3$, each independently, represent hydrogen, $C_1$–$C_4$ lower alkyl, carboxyl or alkoxycarbonyl, X represents $C_1$–$C_4$ lower alkyl, $C_1$–$C_{18}$ alkoxy, halogen, $C_1$–$C_{20}$ acyloxy, acetylamino, trimethylsilyloxy or di($C_1$–$C_4$) alkylaminomethy and the salts thereof, said heterocyclic coupler being present in an amount ranging from 0.05 to 3.5 percent by weight based on the total weight of said second composition and introducing an oxidizing agent containing hydrogen peroxide into said second composition being applied to said fibers in said second step just before application or in a third step, applying to said keratinous fibers an oxidizing agent containing hydrogen peroxide, the combined weight of said oxidation dyestuff precursor and said heterocyclic coupler applied to said fibers ranging from 0.3 to 7 percent based on the total weight of said first and second compositions, wherein said method does not include applying iodide ions to the fibers in an amount capable of oxidizing said oxidation dye precursor and said heterocyclic coupler.

16. In a tinctorial composition for dyeing keratinous fibers which comprises, in a medium suitable for dyeing said fibers, at least one oxidation dyestuff precursor selected from the group consisting of a paraphenylene diamine having formula

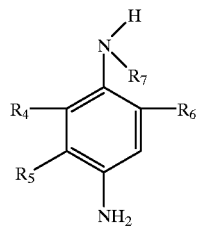

(IV)

wherein $R_4$, $R_5$ and $R_6$, each independently represent hydrogen, halogen, an alkyl having 1–4 carbon atoms or alkoxy having 1–4 carbon atoms, and $R_7$ represents hydrogen, alkyl, carbamylalkyl, mesylaminoalkyl, acetylaminoalkyl, ureidoalkyl, carbalkoxyaminoalkyl, piperidinoalkyl or morpholinoalkyl, wherein said alkyl and alkoxy moieties have 1–4 carbon atoms, and the salt of said paraphenylenediamine, a para-aminophenol, a para-heterocyclic oxidation dye precursor, a bis-phenyl alkylene diamine, an ortho-aminophenol and an ortho-phenylenediamene, and at least one oxidizing agent containing hydrogen peroxide, the improvement comprising including in said composition at least one heterocyclic coupler having the formula

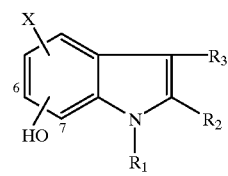

(I)

wherein $R_1$ represents hydrogen or $C_1$–$C_4$ alkyl, $R_2$ and $R_3$, each independently, represent hydrogen, $C_1$–$C_4$ lower alkyl, carboxyl or alkoxycarbonyl, X represents $C_1$–$C_4$ lower alkyl, $C_1$–$C_{18}$ alkoxy, halogen, acetylamino, trimethylsilyloxy or di($C_1$–$C_4$) alkylaminomethyl, the OH group occupying the 6- or 7-positions, and the salts thereof, said heterocyclic coupler being present in an amount ranging from 0.05 to 3.5 percent by weight based on the total weight of said composition, the combined total weight of said oxidation dyestuff precursor and said heterocyclic coupler ranging from 0.3 to 7 weight percent based on the total weight of said composition, said composition being free of any iodide ions in an amount capable of oxidizing said oxidation dyestuff precursor and said heterocyclic coupler of formula I.

17. A tinctorial composition comprising in a medium suitable for dyeing said fibers at least one oxidation dyestuff precursor selected from the group consisting of a paraphenylene diamine having the formula

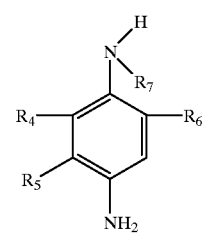

(IV)

wherein $R_4$, $R_5$ and $R_6$, each independently represent hydrogen, halogen, an alkyl having 1–4 carbon atoms or alkoxy having 1–4 carbon atoms, and $R_7$ represents hydrogen, alkyl, carbamylalkyl, mesylaminoalkyl, acetylaminoalkyl, ureidoalkyl, carbalkoxyaminoalkyl, piperidinoalkyl or morpholinoalkyl, wherein said alkyl and alkoxy moieties have 1–4 carbon atoms, and the salt of said paraphenylenediamine, a para-aminophenol, a paraheterocyclic oxidation dye precursor, a bis-phenyl alkylene diamine, an orthoaminophenol and an ortho-phenylenediamene, in combination with at least one heterocyclic coupler having the formula

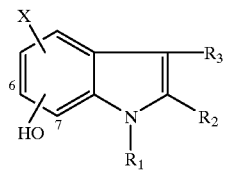 (I)

wherein $R_1$ represents hydrogen or $C_1$–$C_4$ alkyl, $R_2$ and $R_3$, each independently represent hydrogen, $C_1$–$C_4$ lower alkyl, carboxyl or alkoxycarbonyl, X represents $C_1$–$C_4$ lower alkyl, $C_1$–$C_{18}$ alkoxy, halogen, $C_1$–$C_{20}$ acyloxy, acetylamino, trimethylsilyloxy or di($C_1$–$C_4$) alkylaminomethyl the OH group occupying the 6- or 7-positions, and the salts thereof, said heterocyclic coupler being present in an amount ranging from 0.05 to 3.5 percent by weight based on the total weight of said composition, the combined total weight of said oxidation dyestuff precursor and said heterocyclic coupler ranging from 0.3 to 7 weight percent based on the total weight of said composition, and at least one oxidizing agent containing hydrogen peroxide, said composition being free of any iodide ions in an amount capable of oxidizing dyestuff precursor and said heretocyclic coupler of the formula (I).

* * * * *